United States Patent [19]

Graham

[11] 4,031,147
[45] June 21, 1977

[54] PROCESS FOR DIRECTED CHLORINATION OF ALKYLBENZENES

[75] Inventor: John C. Graham, Warren, Mich.

[73] Assignee: Hooker Chemicals & Plastics Corporation, Niagara Falls, N.Y.

[22] Filed: Aug. 1, 1975

[21] Appl. No.: 601,219

[52] U.S. Cl. .................. 260/650 R; 252/429 R; 252/429 A
[51] Int. Cl.² .................................. C07C 25/04
[58] Field of Search ............................ 260/650 R

[56] References Cited

UNITED STATES PATENTS

| 1,741,305 | 12/1929 | Jaeger | 260/650 R |
| 1,946,040 | 2/1934 | Stoesser et al. | 260/650 R |
| 3,226,447 | 12/1965 | Bing et al. | 260/650 R |

*Primary Examiner*—D. Horwitz
*Attorney, Agent, or Firm*—Peter F. Casella; William J. Crossetta, Jr.; Arthur S. Cookfair

[57] ABSTRACT

A process for the production of nuclear chlorinated alkylbenzenes comprises reacting, in the liquid phase, an alkylbenzene with chlorine in the presence of a Lewis acid catalyst and a co-catalyst comprising a thianthrene compound or mixture of thianthrene compounds characterized by the formula:

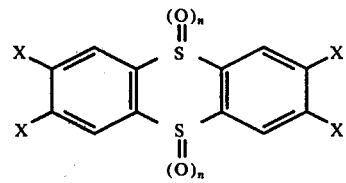

where each $n$ is 0 to 1, and each $x$ is hydrogen or an electron-withdrawing substituent with the proviso that at least one $x$ is an electron withdrawing substituent. The monochlorinated alkylbenzene products prepared in this manner are characterized by a desirably low ratio of ortho to para isomer.

34 Claims, No Drawings

PROCESS FOR DIRECTED CHLORINATION OF ALKYLBENZENES

BACKGROUND OF THE INVENTION

The chemical reaction of chlorine with alkylbenzene, such as toluene, to prepare nuclear substituted chlorocompounds such as monochlorotoluene, is well known and of considerable commercial importance. Such reactions are generally carried out in the presence of a chlorination catalyst such as antimony chloride, ferric chloride, aluminum chloride, and the like. The usual products of such reactions are a mixture of various mono-chlorinated and/or polychlorinated compounds and various positional isomers of these. For example, in the liquid phase substitution-chlorination of toluene, by reaction of chlorine and toluene, to form monochlorotoluene, the usual product is a mixture of orthochlorotoluene and parachlorotoluene which may, in addition, contain varying amounts of other chlorinated products such as metachlorotoluene, dichlorotoluene, polychlorotoluenes and benzylic chlorides. Of the major reaction products, that is orthochlorotoluene and parachlorotoluene, the latter is the most commercially valuable. In the past, considerable effort has been expended in attempts to direct the chlorination reaction in such a manner as to lower the ratio of orthochlorotoluene to parachlorotoluene, that is, to discover reaction conditions under which the formation of parachlorotoluene is favored. Thus, for example, it is known from U.S. Pat. No. 1,946,040 that when alkylbenzenes are reacted with chlorine, the yield of parachlorinated product is improved with the aid of a mixed catalyst comprising sulfur and antimony trichloride and, optionally, iron or lead. In British Pat. No. 1,153,746 (1969) it is disclosed that in the chlorination of toluene in the presence of a ring chlorination catalyst, such as ferric chloride, antimony chloride, and the like, the ratio of orthochloro to parachloro isomers produced may be lowered by the presence of an organic sulfur compound such as thiophene, hexadecylmercaptan, dibenzothiophene or the like. Furthermore, in British Pat. No. 1,163,927 (1969) it is disclosed that the proportion of parachlorotoluene produced may be improved when toluene is chlorinated in the presence of elemental sulfur or an inorganic sulfur compound and a ring-chlorination catalyst such as ferric chloride, aluminum chloride, antimony chloride, zinc chloride, iodine, molybdenum chloride, stannous chloride, zirconium tetrachloride or boron trifluoride. In U.S. Pat. No. 3,226,447, issued Dec. 28, 1965 to Bing et al., it is disclosed that in the substitution-chlorination of benzenes and toluene by chlorine, the ratio of ortho isomer to para isomer in the chlorinated product may be lowered when the reaction is carried out in the presence of an iron, aluminum or antimony halide catalyst and a co-catalyst which is an organic sulfur compound wherein the sulfur is divalent. Examples of such cocatalyst include various mercaptans, mercapto-aliphatic carboxylic acids, aliphatic thiocarboxylic acids, alkyl sulfides, alkyl disulfides, thiophenols, aryl sulfides, aryl disulfides and the like containing divalent sulfur. The use of such co-catalysts in the chlorination of toluene produces a product wherein the ratio of orthochlorotoluene to parachlorotoluene is 1.2, indicating a considerable improvement over the ortho to para isomer ratio achieved in the absence of the co-catalyst. However, it will be apparent that even a 1.2 ratio of ortho to para isomer represents a considerable economic disadvantage in the production of substantial amounts — greater than 50 percent of the monochlorotoluene mixture — of the unwanted ortho isomer. Thus, it will be apparent that a considerable commercial benefit is to be derived from a still further lowering of the ortho to para isomer ratio.

It is an object of the present invention to provide a process for the directed nuclear chlorination of aromatic compounds whereby the formation of parachloro isomers in the chlorinated product is substantially increased. It is a further object to provide a process for the directed nuclear chlorination of alkylbenzens whereby the chlorinated product is characterized by a low ratio of orthochloro to parachloro isomers. It is a further object to provide new catalysts for the para-directed halogenation or aromatic compounds, especially alkylbenzenes. It is a still further object to provide a new catalyst system based on a para-directing co-catalyst comprising a thianthrene compound or mixture thereof.

The thianthrene compounds employed as para-directing co-catalysts in accordance with this invention are described hereinbelow in accordance with the current Chemical Abstracts system whereby the numbering of ring positions is as follows:

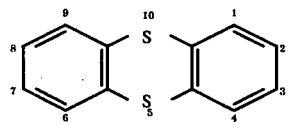

SUMMARY OF THE INVENTION

In accordance with the present invention there is provided a process for the production of nuclear chlorinated alkylbenzenes which comprises reacting, in the liquid phase, an alkylbenzene with chlorine in the presence of a catalyst system comprising a Lewis acid catalyst and a co-catalyst comprising a thianthrene compound or mixture of thianthrene compounds characterized by the formula:

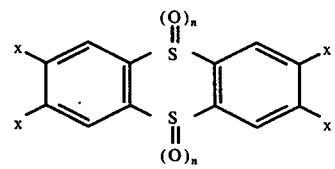

where each $n$ is 0 to 1, and each $x$ is hydrogen or an electron-withdrawing substituent with the proviso that at least one $x$ is an electron-withdrawing substituent.

A wide variety of known Lewis acid catalysts may be employed in the process of the present invention. The term "Lewis acid catalyst" as employed herein includes, in addition to Lewis acids, those compounds or elements that will form or function as Lewis acids under the conditions of the chlorination reaction. Preferred catalysts for this purpose are compounds of antimony, lead, iron, molybdenum and aluminum, including for example, the halides, oxyhalides, oxides, sulfides, sulfates, carbonyls and elemental form of these elements and mixtures of such compounds and most preferably the chlorides, oxychlorides, oxides and elemental forms of antimony and iron. Typical of the catalysts which may be employed in the process of this invention are aluminum chloride, antimony trichloride, antimony pentachloride, antimony trioxide, antimony tetraoxide, antimony pentaoxide, antimony trifluoride, antimony oxychloride, molybdenum hexacarbonyl, lead sulfide, ferric chloride, ferrous chloride, ferrous sulfate, ferric oxide, ferrous sulfide, iron disulfide, iron pentacarbonyl, iron metal, and the like.

The thianthrene co-catalysts suitable for use in the process of this invention are characterized by the formula shown hereinabove and include, for example, thianthrene compounds, as well as the analogous mono- or disulfoxide compounds, wherein one or more electron-withdrawing substituents are present in the positions designated, as well as mixtures of such compounds. When more than one electron-withdrawing substituent is present on the thianthrene nucleus, the substituents may be the same or different. Suitable electron-withdrawing substituents which may be present on the thianthrene or thianthrene oxide nucleus in the $x$ positions include for example, halo-, alkanoyl-, aroyl-, nitro-, sulfonyl-, cyano-, quarternary amino-groups and the like, the preferred electron-withdrawing substituents being chloro-, fluoro-, bromo-, acetyl-, and benzoyl.

The preferred co-catalysts are thianthrene compounds characterized by the formula shown hereinabove where $n$ is 0, and at least two of the designated X substituents are electron-withdrawing substituents. Most preferred are the halo-thianthrenes and in particular the chlorothianthrenes or mixtures of chlorothianthrenes characterized by the above formula. Particularly preferred is 2,3,7,8-tetrachlorothianthrene, which may be employed alone or as a component of a mixture of chlorothianthrenes.

Halothianthrenes, such as mono-, di-, tri-, or tetra-halothianthrene including mixtures thereof, may be employed as co-catalysts in the process of the present invention. The preferred halothianthrenes are chlorothianthrenes wherein the chloro-substituent is present on one or more of the positions para to the sulfur atoms or mixtures of such isomers, which may be characterized by the formula:

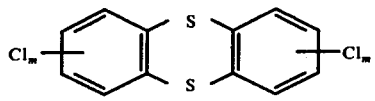

wherein $m$ is about 1 to about 2.5 and wherein at least some and preferably most of the chloro-substituents are present on the thianthrene nucleus in positions para- to a sulfur atom. It is preferred, though not essential, that such chlorothianthrene mixtures contain as a component thereof, 2,3,7,8-tetrachlorothianthrene. It has been found that the presence of a chloro or other electron-withdrawing substituent on the peri-positions, that is, positions 1,4,6 and 9, adjacent to the sulfur atoms, tends to inhibit or lessen the para-directing effect of the thianthrene cocatalyst. Nevertheless, where mixtures of chlorothianthrenes are employed, compounds such as octachlorothianthrene, heptachlorothianthrene, hexachlorothianthrene, pentachlorothianthrene, and others wherein a chlorine is present on one or more of the peri-positions, may be present in the mixture, preferably only as a minor component thereof. Similarly, when mixtures of other thianthrene compound co-catalysts of the present invention are employed, compounds having substituents in the peri-positions may be present, preferably only as a minor component of such mixture.

Mixtures of chlorothianthrenes, useful as para-directing co-catalysts in accordance with this invention may be prepared by chlorination of thianthrene in the presence of a Lewis acid catalyst. When thianthrene is chlorinated in this manner, chlorine substitution occurs preferentially at ring positions para to a sulfur atom that is at the 2,3,7, and 8 positions. Details regarding the preparation of chlorothianthrene mixtures, as well as the compound 2,3,7,8-tetrachlorothianthrene, are disclosed in co-pending application Ser. No. 601,218, filed Aug. 1, 1976.

The amount of catalyst and co-catalyst employed may vary considerably. Thus substantial benefits in terms of the lowering of the ratio of ortho- to para-isomer in the product may be achieved when the catalyst and co-catalyst are present in a total amount ranging of from less than 0.01 percent to five percent by weight or more, based on the weight of alkylbenzene, and preferably in a molar ratio of catalyst:co-catalyst of about 0.1:1 to about 10:1. However, based on effectiveness as well as economic considerations, it is preferred to employ the catalyst and co-catalyst in a total amount of about 0.01 to about 2.0 weight percent, based on the weight of alkylbenzene and in a molar ratio of catalyst:co-catalyst of about 0.25:1 to about 1:1.

Under atmospheric pressure, the chlorination reaction of the present invention may be carried out over a wide range of temperatures, ranging for example from sub-zero temperatures (Celsius scale) to over 100° C. For example, in the chlorination of toluene in the presence of a Lewis acid catalyst (SbCl$_3$) and thianthrene compound co-catalyst (a chlorothianthrene mixture) the chlorination was found to proceed readily at temperatures as low as −25° C to produce a monochlorotoluene product having a desirably low ortho:-para isomer ratio. (Below about −25° C, little or no reaction occurs.) The upper limit of temperature is, of course, determined by the boiling point of the reaction mixture, and may, depending on the boiling point limitation, range as high as 150° C or higher. However, no practical advantage is gained through the use of higher temperatures and it is preferred to utilize temperatures in the range of about 0° C to about 125° C, and most preferably in the range of about 20° C to about 70° C. Although it is preferred to carry out the process at atmospheric pressures, subatmospheric or superatmospheric pressures may be employed if desired.

The alkylbenzenes which may be chlorinated in accordance with the present invention include the various straight chain and branched chain alkylbenzenes as well as substituted alkylbenzenes. The preferred alkyl benzenes are those wherein the alkyl group is 1 to 4 carbon atoms, and most preferably toluene. In the chlorination of toluene in accordance with this invention, monochlorotoluene products having a ratio of ortho-chlorotoluene/parachlorotoluene of less than about 1.0 are obtainable. It will be appreciated that, although the preparation of monochloro alkylbenzenes, having a relatively high proportion of parachloro alkylbenzene, is an important object of the present invention, the monochloro product may be further chlorinated, if desired, to produce higher chlorinated derivatives.

The process of this invention may be carried out by chlorination of the alkylbenzene in solution or in the absence of a solvent. Suitable solvents which may be employed, if desired, include for example various halogenated solvents such as carbon tetrachloride, or aromatic solvents such as monochlorobenzene. It is preferred, however, to carry out the chlorination directly, in the absence of a solvent.

The following specific examples are provided to further illustrate this invention and the manner in which it may be carried out. It will be understood, however, that the specific details given in the examples have been chosen for purpose of illustration and are not to be construed as a limitation on the invention. In the examples, unless otherwise indicated, all parts and percentages are by weight and all temperatures are in degrees Celsius.

EXAMPLE 1

A mixture of 300 parts of toluene, 3.0 parts of 2,3,7,8-tetrachlorothianthrene, and 1.95 parts of antimony trichloride was charged to a reaction vessel and heated to about 50° C. The temperature was maintained at about 50° C while 208.0 parts of chlorine gas was introduced into the reaction mixture over a period of about 5 hours, 45 minutes.

The reaction product was analyzed by gas chromtographic methods and found to contain approximately 7.8% toluene; 24.7% orthochlorotoluene and 49.6% parachlorotoluene. No benzylic products were present. The ratio of ortho:para isomer was 0.86.

EXAMPLE 2

A reaction mixture was prepared as in Example 1 except that only 1.5 parts of antimony trichloride catalyst and 3.0 parts of the tetrachlorothianthrene co-catalyst was employed. The temperature was maintained at about 50° C while 208 parts of chlorine gas was introduced into the reaction mixture over a period of about 5 hours, 35 minutes. The reaction product contained 26.0% toluene; 34.0% orthochlorotoluene; 40.0% parachlorotoluene and no benzylic products. The ratio of ortho-para isomer was 0.85.

EXAMPLES 3-8

A series of chlorothianthrene compounds and mixtures, having varying average amounts of nuclear substituted chlorine, were prepared and used as para-directing co-catalysts in the process of the present invention. The chlorothianthrene mixtures were prepared by a liquid phase chlorination of thianthrene. In the mixtures employed the chlorine substituents are present predominently at the ring positions para to the sulfur atoms. Details of the preparation of chlorothianthrene mixtures are disclosed in detail in the aforementioned co-pending application, Ser. No. 601,218, filed Aug. 1, 1976.

The examples disclose the effectiveness of various chlorothianthrene compounds and mixtures in the chlorination of toluene to monochlorotoluene having a desirably low ortho:para isomer ratio. In the examples, the reactants toluene, chlorothianthrene, and antimony chloride, in the amounts shown were charged to a reaction vessel and heated to about 50° C. The temperature was maintained at about 50°-55° C while chlorine gas, in the amounts shown, was introduced into the reaction mixture over a period of about 3-6 hours. The reaction product was analyzed by gas chromatographic techniques with the results as shown.

EXAMPLE 3

The para-direction co-catalyst was a chlorothianthrene mixture characterized by the formula:

| Reactants | Amount (Parts by weight) |
| --- | --- |
| Toluene | 300 |
| Chlorothianthrene Mixture (as shown above) | 1.5 |
| SbCl$_3$ | 1.0 |
| Cl$_2$ | 208 |

The monochlorotoluene reaction product contained less than 10 percent toluene and no benzylic products. The ratio of ortho:para isomers was 1.06.

EXAMPLE 4

The para-directing co-catalyst was 2,7-dichlorothianthrene (m.p.=178.5-180°C).

| Reactants | Amount (Parts by weight) |
| --- | --- |
| Toluene | 300 |
| Chlorothianthrene | 0.3 |
| SbCl$_3$ | 0.08 |
| Cl$_2$ | 195-210 |

The reaction product consisted predominantly of orthochlorotoluene and parachlorotoluene in a ratio of ortho:para isomer of 0.79.

EXAMPLE 5

The para-directing co-catalyst was a chlorothianthrene mixture having a melting point in the range 93°-107° C and characterized by the formula:

| Reactants | Amount (Parts by weight) |
| --- | --- |
| Toluene | 300 |
| Chlorothianthrene | .30 |
| SbCl$_3$ | .20 |
| Cl$_2$ | 116 |

The reaction was stopped after slightly more than one-half the stoichiometric amount of chlorine had been fed to the reaction medium. The reaction product consisted of about 41.1 percent toluene 27.8 percent orthochlorotoluene, and 31.1 percent parachlorotoluene. The ratio of ortho:para isomers was 0.83.

EXAMPLE 6

The para-directing co-catalyst was a chlorothianthrene mixture having a melting point in the range of 162°-237° and characterized by the formula:

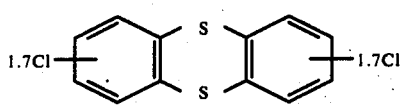

| Reactants | Amount (Parts by weight) |
| --- | --- |
| Toluene | 300.0 |
| Chlorothianthrene | 0.3 |
| SbCl₃ | 0.2 |
| Cl₂ | 208 |

The reaction product contained about 9.5 percent toluene, 42.6 percent orthochlorotoluene, and 48 percent parachlorotoluene. The ratio of ortho:para isomers was 0.83.

EXAMPLE 7

The para-directing co-catalyst was a chlorothianthrene mixture having a melting point in the range of 235°–252° C and characterized by the formula:

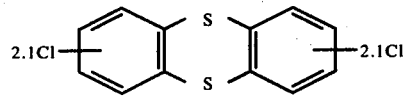

| Reactants | Amount (Parts by weight) |
| --- | --- |
| Toluene | 92.1 |
| Chlorothianthrene | .046 |
| SbOCl | .0245 |
| Cl₂ | 26.0 |

The reaction product contained 63.3 percent toluene, 17.1 percent orthochlorotoluene and 19.7 percent parachlorotoluene. The ratio of ortho:para isomers was 0.87.

EXAMPLE 8

The para-directing co-catalyst was a chlorothianthrene mixture having a melting point range of 247°–263° C and characterized by the formula:

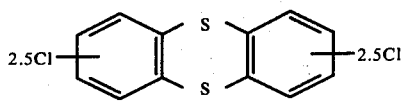

| Reactants | Amount (Parts by Weight) |
| --- | --- |
| Toluene | 300.0 |
| Chlorothianthrene | .60 |
| SbCl₃ | .40 |
| Cl₂ | 232.0 |

The reaction product contained about 17.7 percent toluene, 38.9 percent orthochlorotoluene, 43.4 percent parachlorotoluene. The ratio of ortho:para isomers was 0.9.

EXAMPLES 9–14

The following Examples 9–14 illustrate the use of various thianthrene compounds as co-catalysts in the chlorination of toluene. The chlorination reactions were run under substantially similar conditions to those employed in Examples 1–8 employing the catalyst and co-catalyst in the amounts shown herein below to obtain a monochlorotoluene product having an ortho:para isomer ratio as shown. The percent catalyst and co-catalyst is based on the weight of toluene.

| Ex. | Co-Catalyst | % by Weight | Catalyst | % by Weight | Ortho/Para Ratio |
| --- | --- | --- | --- | --- | --- |
| 9. | difluoro-substituted thianthrene | 0.11 | SbCl₃ | 0.49 | 0.86 |
| 10. | monobromo-substituted thianthrene | 0.5 | FeCl₃ | 0.25 | 0.98 |
| 11. | dibromo-substituted thianthrene | 0.1 | SbCl₃ | .024 | 0.89 |
| 12. | tetrabromo-substituted thianthrene | 0.5 | SbCl₃ | 0.3 | 0.82 |
| 13. | diacetyl-substituted thianthrene | 0.11 | SbCl₃ | .04 | 0.89 |
| 14. | dibenzoyl-substituted thianthrene | 0.11 | SbCl₃ | .04 | 0.80 |

EXAMPLES 15-44

The following Examples (15-44) set forth the ratio of orthochlorotoluene to parachlorotoluene (ortho:para) obtained when toluene is chlorinated as in the previous Examples, in the presence of a catalyst system consisting of 2,3,7,8-tetrachlorothianthrene co-catalyst and various Lewis acid catalysts. In these Examples tetrachlorothianthrene was employed in the amount of about 1.0 percent by weight based on the amount of starting toluene in the reaction mixture and the Lewis acid catalyst was employed in molar proportion as shown.

| Example | Catalyst | Molar Ratio of Catalyst:Co-Catalyst | Ortho:Para Obtained |
|---|---|---|---|
| 15 | FeCl$_3$ | 1.0 | 0.80 |
| 16 | FeCl$_3$ | 0.5 | 0.84 |
| 17 | FeCl$_3$ | 0.25 | 0.84 |
| 18 | Fe | 1.0 | 0.84 |
| 19 | Fe | 0.5 | 0.83 |
| 20 | Fe | 0.25 | 0.83 |
| 21 | Fe$_2$O$_3$ | 1.0 | 1.13 |
| 22 | Fe$_2$O$_3$ | 0.5 | 0.85 |
| 23 | Fe$_2$O$_3$ | 0.25 | 0.87 |
| 24 | FeCl$_2$ | 0.5 | 0.84 |
| 25 | FeS | 1.0 | 0.83 |
| 26 | FeS | 1.5 | 0.83 |
| 27 | FeS | 2.0 | 0.85 |
| 28 | FeS | 3.0 | 0.88 |
| 29 | Fe(CO)$_5$ | 0.5 | 0.92 |
| 30 | PbS | 0.5 | 0.84 |
| 31 | PbS | 1.0 | 0.88 |
| 32 | W(CO)$_6$ | 0.5 | 0.99 |
| 33 | SnCl$_4$ | 0.5 | 1.0 |
| 34 | Sb$_2$O$_3$ | 1.0 | 0.81 |
| 35 | Sb$_2$O$_3$ | 0.5 | 0.81 |
| 36 | Sb$_2$O$_3$ | 0.25 | 0.79 |
| 37 | SbCl$_5$ | 1.0 | 0.95 |
| 38 | SbCl$_5$ | 0.5 | 1.06 |
| 39 | SbCl$_5$ | 0.25 | 0.79 |
| 40 | Sb$_2$O$_4$ | 1.0 | 0.95 |
| 41 | SbF$_3$ | 0.5 | 0.86 |
| 42 | SbF$_3$ | 0.25 | 0.79 |
| 43 | Mo(CO)$_6$ | .5 | 0.80 |
| 44* | AlCl$_3$ | 1.0 | 1.01 |

*0.5 percent tetrachlorothianthrene

Analysis of the products obtained in Examples 15-44 indicated trace amounts of benzyl chloride in the product of Example 30. The remaining Examples contained no detectable benzyl chlorides.

EXAMPLE 45

A reaction mixture of 50.6 parts of toluene, 0.091 parts of antimony trichloride and 0.25 parts of 2,7-dichlorothianthrene sulfoxide (B-isomer).

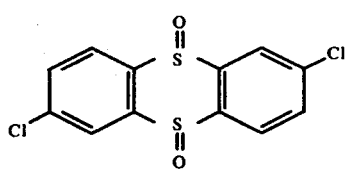

was charged to a reaction vessel and heated to about 50° C. The temperature was maintained at about 50°-55° to while 22 parts of Cl$_2$ was introduced into the reaction mixture over about a 3-hour period. The monochlorotoluene product was analyzed by gas chromatographic techniques and found to have a ratio of ortho:para isomers of 0.87. No benzyl chlorides were detected.

EXAMPLE 46

A reaction mixture of 92.1 parts of toluene, 0.0414 parts of antimony trichloride and 0.23 parts of 2,7-dichlorothianthrene sulfoxide ($\alpha$-isomer) was charged to a reaction vessel and heated to about 50° C. The temperature was maintained at about 50° C while 36 parts of Cl$_2$ was introduced over about a 3 hour period. The monochlorotoluene product was analyzed by gas chromatographic techniques and formed to have a ratio of ortho:para isomer of 0.96. A trace of benzyl chloride was detected.

EXAMPLE 47

The procedure of Example 46 was repeated except that 0.165 parts of antimony trichloride and 0.46 parts of the 2,7-dichlorothianthrene sulfoxide were employed. The ratio of ortho:para isomer obtained was 1.01. A trace of benzyl chloride was detected.

EXAMPLE 48

A mixture of 106.2 parts of ethylbenzene, 0.106 parts of tetrachlorothianthrene, and 0.0185 parts of antimony trichloride was charged to a reaction vessel heated to a temperature of about 50° C. The temperature was maintained at about 50° C while 65 parts of chlorine gas was introduced into the reaction mixture over a period of about 5 hours, 30 minutes. The reaction product contained orthochloroethylbenzene and parachloroethylbenzene in a ratio of ortho:para isomers of about 0.60.

EXAMPLE 49

A mixture of 106.2 parts of cumene, 0.106 parts of tetrachlorothianthrene, and 0.0185 parts of antimony trichloride was charged to a reaction vessel and heated to a temperature of about 50° C. The temperature was maintained in a range of about 50° to 65° C while 56 parts of chlorine gas was introduced into the reaction mixture over a period of about 4 hours, 45 minutes. The reaction product contained orthochlorocumene and parachlorocumene in a ratio of ortho:para isomers of about 0.44.

For purposes of comparison, Examples 50 and 51, below, set forth the results obtained when thianthrene compounds having electron-withdrawing substituents in the peri-position are employed as co-catalysts.

EXAMPLE 50

A mixture of 92.1 parts of toluene 0.46 parts of hexachlorothianthrene, and 0.32 parts of antimony trichloride was charged to a reaction vessel and heated to about 50° C. The temperature was maintained at about 50° C while 65 parts of chlorine was introduced into the reaction mixture over a period of about 3 hours. The reaction product was analyzed by gas chromatographic methods and found to contain approximately 14.4% toluene; 47.4% orthochlorotoluene; and 38.2% parachlorotoluene. The ratio of ortho:para isomer was 1.39.

EXAMPLE 51

The procedure of Example 50 was repeated except that the following reactants were employed in the amounts shown:

| Reactants | Amount (Parts by Weight) |
|---|---|
| Toluene | 92.1 |
| Octachlorothianthrene | 0.1 |
| SbCl₃ | 0.023 |
| Cl₂ | 63.0 |

The monochlorotoluene product obtained was characterized by a ratio of ortho:para isomers of 1.60.

As will be seen from Examples 50 and 51, thianthrene compounds such as hexachlorothianthrene and octachlorothianthrene, having electron withdrawing substituents at the peri-position, that is, adjacent to the sulfur atom, are notably less effective as para-directing co-catalysts in the chlorination of alkylbenzenes. Nevertheless, such compounds may be present, preferably as a minor component, of the chlorothianthrene mixtures employed as co-catalysts in accordance with the present invention.

What is claimed is:

1. A process for the preparation of nuclear chlorinated alkylbenzenes which comprises reacting an alkylbenzene with chlorine at a temperature of about −25° to about 150° Celsius and in the presence of a Lewis acid catalyst and a co-catalyst comprising a thianthrene compound or mixture of thianthrene compounds characterized by the formula:

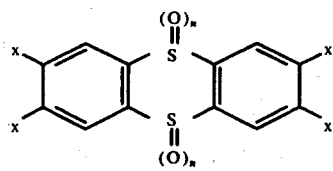

where each $n$ is 0 to 1 and each $x$ is hydrogen or an electron-withdrawing substituent with the proviso that at least one $x$ is an electron-withdrawing substituent.

2. A process according to claim 1 wherein said electron-withdrawing substituent is selected from the group consisting of halo-, alkanoyl-, aroyl-, nitro-, sulfonyl-, cyano-, and quarternary amino-.

3. A process according to claim 2 wherein the alkyl group of said alkylbenzene is a branched or straight chain alkyl group of 1 to 4 carbon atoms and the alkylbenzene is reacted with chlorine at a temperature of about −25° to about 150° Celsius, and said catalyst and co-catalyst are present in an amount of about 0.01 to about 5.0 weight percent, based on the weight of alkylbenzene and in a molar ratio of catalyst: co-catalyst of about 0.1:1 to about 10:1.

4. A process according to claim 3. wherein the Lewis acid catalyst is a halide, oxyhalide, oxide, sulfide, sulfate, carbonyl or elemental form of antimony, lead, iron, molybdenum, or aluminum.

5. A process according to claim 4 wherein the co-catalyst is a thianthrene compound or mixture of thianthrene compounds characterized by the formula shown wherein $n$ is 1.

6. A process according to claim 5 wherein the alkylbenzene is toluene.

7. A process according to claim 5 wherein the co-catalyst is a thianthrene compound or mixture of thianthrene compounds characterized by the formula shown wherein said electron-withdrawing substituent is chloro-.

8. A process according to claim 7 wherein the Lewis acid catalyst is antimony trichloride.

9. A process according to claim 8 wherein the co-catalyst is 2,7-dichlorothianthrene sulfoxide.

10. A process according to claim 4 wherein the co-catalyst is a thianthrene compound or mixture of thianthrene compounds characterized by the formula shown, wherein $n$ is 0.

11. A process according to claim 10 wherein the Lewis acid catalyst is a chloride, oxychloride, oxide or elemental form of antimony or iron.

12. A process according to claim 11 wherein the co-catalyst is a thianthrene compound or mixture of thianthrene compounds characterized by the formula shown wherein said electron-withdrawing substituent is chloro-, fluoro-, bromo-, benzoyl-, or acetyl-.

13. A process according to claim 12 wherein the alkylbenzene is toluene.

14. A process according to claim 13 wherein the Lewis acid catalyst is antimony trichloride.

15. A process according to claim 14 wherein the co-catalyst is a thianthrene compound or mixture of thianthrene compounds characterized by the formula shown wherein said electron-withdrawing substituent is acetyl-.

16. A process according to claim 14 wherein the co-catalyst is a thianthrene compound or mixture of thianthrene compounds characterized by the formula shown wherein said electron-withdrawing substituent is benzoyl-.

17. A process according to claim 14 wherein the co-catalyst is a thianthrene compound or mixture of thianthrene compounds characterized by the formula shown wherein said electron-withdrawing substituent is bromo-.

18. A process according to claim 14 wherein the co-catalyst is a thianthrene compound or mixture of thianthrene compounds characterized by the formula shown wherein said electron-withdrawing substituent is fluoro-.

19. A process according to claim 10 wherein the co-catalyst is a thianthrene compound or mixture of thianthrene compounds characterized by the formula shown wherein said electron-withdrawing substituent is chloro-.

20. A process according to claim 19 wherein the Lewis acid catalyst is a chloride, oxychloride, oxide or elemental form of antimony or iron.

21. A process according to claim 20 wherein the alkylbenzene is toluene.

22. A process according to claim 21 wherein the co-catalyst is 2,7dichlorothianthrene.

23. A process according to claim 20 wherein the co-catalyst is 2,3,7,8-tetrachlorothianthrene.

24. A process according to claim 23 wherein the alkylbenzene is toluene.

25. A process according to claim 24 wherein the Lewis acid catalyst is antimony trichloride.

26. A process according to claim 20 wherein the co-catalyst is a mixture of thianthrene compounds characterized by the formula:

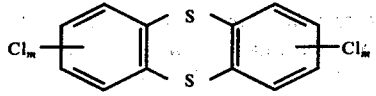

where *m* is about 1 to about 2.5, and at least some of the chlorosubstituents are present in the thianthrene nucleus in positions para- to a sulfur atom.

27. A process according to claim 26 wherein at least a portion of said mixture of thianthrene compounds is 2,3,7,8-tetrachlorothianthrene.

28. A process according to claim 27 wherein the catalyst and cocatalyst are present in an amount of about 0.01 to about 2.0 weight percent, based on the weight of alkylbenzene, and the molar ratio of catalyst-:co-catalyst is about 0.1:1 to about 10.1.

29. A process according to claim 28 wherein the alkylbenzene is toluene.

30. A process according to claim 29 wherein the Lewis acid catalyst is antimony trichloride.

31. A process according to claim 29 wherein the Lewis acid catalyst is ferric chloride.

32. A process according to claim 29 wherein the Lewis acid catalyst is elemental iron.

33. A process for the nuclear chlorination of toluene which comprises reacting toluene with chlorine at a temperature of about 20° to about 60° Celsius in the presence of about 0.01 to about 2.0 weight percent, based on toluene, of a catalyst system consisting essentially of antimony trichloride and a mixture of thianthrene compounds characterized by the formula:

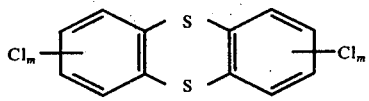

where *m* is about 1 to about 2.5 and wherein at least a portion of said mixture is 2,3,7,8-tetrachlorothianthrene, the molar ratio of antimony trichloride to thianthrene compounds being about 0.25:1 to about 1:1.

34. A process according to claim 33 wherein said mixture of thianthrene compounds contains 2,3,7,8-tetrachlorothianthrene as a major component thereof.

* * * * *

UNITED STATES PATENT OFFICE
CERTIFICATE OF CORRECTION

PATENT NO. : 4,031,147
DATED : June 21, 1977
INVENTOR(S) : John C. Graham

It is certified that error appears in the above-identified patent and that said Letters Patent are hereby corrected as shown below:

Column 2, line 13, "alkylbenzens " should read --alkylbenzenes--.
Column 3, line 34, 'employed along or as" should read --employed alone or as--.  Column 5, line 29, "24.7%" should read --42.7%--.  Column 9, line 62, "50°-55° to while" should read --50°-55° while--.  Column 13, line 11, "10.1." should read --10:1. --.

Signed and Sealed this

Fourth Day of October 1977

[SEAL]

Attest:

RUTH C. MASON
*Attesting Officer*

LUTRELLE F. PARKER
*Acting Commissioner of Patents and Trademarks*